(12) United States Patent
Glendenning

(10) Patent No.: US 12,165,781 B2
(45) Date of Patent: Dec. 10, 2024

(54) X-RAY IMAGING SYSTEM COMPRISING A SHUTTER AND METHOD

(71) Applicant: ROBOTIC TECHNOLOGIES LIMITED, Dunedin (NZ)

(72) Inventor: Roger William Glendenning, Dunedin (NZ)

(73) Assignee: ROBOTIC TECHNOLOGIES LIMITED, Dunedin (NZ)

( * ) Notice: Subject to any disclaimer, the term of this patent is extended or adjusted under 35 U.S.C. 154(b) by 0 days.

(21) Appl. No.: 17/439,746

(22) PCT Filed: Feb. 27, 2020

(86) PCT No.: PCT/NZ2020/050017
§ 371 (c)(1),
(2) Date: Sep. 15, 2021

(87) PCT Pub. No.: WO2020/190153
PCT Pub. Date: Sep. 24, 2020

(65) Prior Publication Data
US 2022/0179299 A1    Jun. 9, 2022

(30) Foreign Application Priority Data

Mar. 15, 2019    (NZ) .......................... 751728

(51) Int. Cl.
*G01N 23/04*    (2018.01)
*G01N 23/046*    (2018.01)
(Continued)

(52) U.S. Cl.
CPC .......... *G21K 1/043* (2013.01); *G01N 23/046* (2013.01); *G03B 42/028* (2013.01); *G21K 1/025* (2013.01); *G21K 1/04* (2013.01); *G03B 2207/00* (2013.01)

(58) Field of Classification Search
CPC ......... A61B 6/022; A61B 6/032; A61B 6/035; A61B 6/04; A61B 6/0464; A61B 6/06;
(Continued)

(56) References Cited

U.S. PATENT DOCUMENTS 4,641,335 A * 2/1987 Hahn ....................... A61B 6/08
976/DIG. 428
4,686,695 A * 8/1987 Macovski .............. A61B 6/482
378/146

(Continued)

FOREIGN PATENT DOCUMENTS

CN    202537523 U    11/2012
GB    135 540 A    11/1919
(Continued)

OTHER PUBLICATIONS

International Search Report and Written Opinion for PCT/NZ2020/050017 (May 26, 2020).
(Continued)

*Primary Examiner* — Allen C. Ho
(74) *Attorney, Agent, or Firm* — Merchant & Gould P.C.

(57) ABSTRACT

An X-ray imaging system includes an X-ray detector; a plurality of X-ray sources configured to illuminate the X-ray detector from different perspectives; a shutter in a transmission plane between each X-ray source controlling transmission of X-rays from each X-ray source to the X-ray detector; and a processor configured to receive and process X-ray data from the X-ray detector. The shutter may be configured to illuminate the X-ray detector alternately with each X-ray source. The processor may determine 3D information about an object from the processed X-ray data. Also provided are methods for processing X-ray data and different embodiments of shutters to alternately illuminate X-ray detectors.

18 Claims, 11 Drawing Sheets

(51) Int. Cl.
*G01N 23/087* (2018.01)
*G03B 42/02* (2021.01)
*G21K 1/02* (2006.01)
*G21K 1/04* (2006.01)

(58) Field of Classification Search
CPC ....... A61B 6/4007; A61B 6/4078; A61B 6/42; A61B 6/4208; A61B 6/4233; A61B 6/4241; A61B 6/44; A61B 6/4429; A61B 6/4435; A61B 6/486; A61B 6/487; A61B 6/508; A61B 6/025; A61B 6/4452; A61B 6/4464; G01N 23/04; G01N 23/046; G01N 23/083; G01N 23/087; G01N 23/10; G01N 23/16; G01N 23/18; G01N 23/043; G01N 23/044; G21K 1/02; G21K 1/025; G21K 1/04; G21K 1/043; G21K 1/046
USPC .......... 378/9, 10, 41, 42, 53, 54, 57, 58, 62, 378/145–153, 19–26
See application file for complete search history.

(56) References Cited

U.S. PATENT DOCUMENTS

| | | | |
|---|---|---|---|
| 4,696,022 A | 9/1987 | Sashin et al. | |
| 5,054,041 A | 10/1991 | Hampel | |
| 5,247,561 A | 9/1993 | Kotowski | |
| 5,359,639 A | 10/1994 | Saito | |
| 5,966,422 A * | 10/1999 | Dafni | A61B 6/482 378/15 |
| 6,125,167 A * | 9/2000 | Morgan | H01J 35/10 378/124 |
| 6,151,381 A * | 11/2000 | Grodzins | G01V 5/222 378/57 |
| 6,229,870 B1 | 5/2001 | Morgan | A61B 6/4014 378/4 |
| 6,449,333 B1 * | 9/2002 | Yamasaki | A61B 6/504 378/42 |
| 6,647,092 B2 * | 11/2003 | Eberhard | G21K 1/04 378/65 |
| 6,731,716 B2 * | 5/2004 | Mihara | A61B 6/032 378/4 |
| 6,760,399 B2 * | 7/2004 | Malamud | A61B 6/4014 378/4 |
| 6,876,719 B2 * | 4/2005 | Ozaki | A61B 6/032 378/7 |
| 6,904,122 B2 | 6/2005 | Swift et al. | |
| 6,914,959 B2 * | 7/2005 | Bailey | A61B 6/482 378/65 |
| 6,990,175 B2 * | 1/2006 | Nakashima | A61B 6/032 378/92 |
| 7,016,455 B2 * | 3/2006 | Bruder | A61B 6/032 378/197 |
| 7,035,371 B2 * | 4/2006 | Boese | A61B 6/022 378/62 |
| 7,039,153 B2 * | 5/2006 | Bruder | G01N 23/046 378/9 |
| 7,085,343 B2 * | 8/2006 | Shinno | A61B 6/4014 378/92 |
| 7,206,373 B2 * | 4/2007 | Seufert | A61B 6/4014 378/4 |
| 7,209,538 B2 * | 4/2007 | Sukovic | A61B 34/30 378/197 |
| 7,233,644 B1 * | 6/2007 | Bendahan | G01N 23/046 378/57 |
| 7,440,540 B2 * | 10/2008 | Kano | A61B 6/022 378/147 |
| 7,639,774 B2 * | 12/2009 | De Man | G21K 1/025 378/124 |
| 7,809,101 B2 * | 10/2010 | Frutschy | H05G 1/025 378/124 |
| 7,809,102 B2 * | 10/2010 | Brada | A61B 6/463 378/20 |
| 7,826,585 B2 * | 11/2010 | Proksa | G01T 1/1647 378/5 |
| 7,844,032 B2 * | 11/2010 | Vermilyea | H01J 35/16 378/9 |
| 7,869,561 B2 * | 1/2011 | Dafni | H05G 1/70 378/19 |
| 7,933,378 B2 * | 4/2011 | Proksa | A61B 6/4014 378/9 |
| 7,949,089 B2 * | 5/2011 | Dafni | A61B 6/481 378/9 |
| 7,976,218 B2 * | 7/2011 | Vermilyea | H01J 35/16 378/124 |
| 8,180,017 B2 * | 5/2012 | Forthmann | H01J 35/10 378/156 |
| 8,270,562 B2 * | 9/2012 | Sainath | A61B 6/4429 378/124 |
| 8,576,989 B2 * | 11/2013 | Kaminski | G01V 5/0025 378/160 |
| 8,908,826 B2 * | 12/2014 | Bernhardt | A61B 6/50 378/42 |
| 9,014,339 B2 * | 4/2015 | Grodzins | G21K 1/043 378/146 |
| 9,020,103 B2 * | 4/2015 | Grodzins | G21K 1/046 378/146 |
| 9,049,996 B2 * | 6/2015 | Tsujii | A61B 6/4007 |
| 9,076,565 B2 * | 7/2015 | Shiraki | G01N 23/046 |
| 9,989,483 B2 * | 6/2018 | Georgeson | G01N 23/20008 |
| 10,153,060 B2 * | 12/2018 | Haunschild | G21K 1/04 |
| 10,714,227 B2 * | 7/2020 | Aaron | G21K 1/02 |
| 11,471,119 B2 * | 10/2022 | Sato | G01N 23/2206 |
| 2002/0126796 A1 | 9/2002 | Yamasaki | |
| 2008/0095308 A1 | 4/2008 | Kano | |
| 2009/0184261 A1 | 7/2009 | Ein-Gal | |
| 2010/0166140 A1 | 7/2010 | Proksa | |
| 2014/0140484 A1 | 5/2014 | Shiraki et al. | |
| 2016/0211044 A1 | 7/2016 | Haunschild | |

FOREIGN PATENT DOCUMENTS

| | | |
|---|---|---|
| WO | 2008/010732 A1 | 1/2008 |
| WO | 2011/115927 A2 | 9/2011 |

OTHER PUBLICATIONS

International Preliminary Report on Patentability for PCT/NZ2020/050017 (Mar. 26, 2021).
Hardin et al., "X-ray Imaging Delivers a Better Cut", Vision Systems Design Magazine, 2011.
European Search Report for EP Application No. 20773460.9 (Apr. 7, 2022).
Examination Report issued in the related European patent application No. 20773460.9, Nov. 27, 2023.

* cited by examiner

X-RAY IMAGING SYSTEM COMPRISING A SHUTTER AND METHOD

This application is a National Stage Application of PCT/NZ2020/050017, filed Feb. 27, 2020, which claims benefit of priority to Patent Application No. 751728, filed Mar. 15, 2019 in New Zealand, which applications are incorporated herein by reference. To the extent appropriate, a claim of priority is made to each of the above disclosed applications.

FIELD

This invention relates to an X-ray imaging system, its method of operation and a shutter used in the system. The method and system are particularly suited to imaging carcasses during meat processing.

BACKGROUND

Imaging an object using X-rays allows non-invasive imaging of the internal components or elements of that object. If the same object is imaged from two different perspectives, a stereoscopic or stereographic pair of images can be produced. A pair of such images can be used to generate 3D coordinate data (i.e. x data (width), y data (height) and z data (depth)) of points of interest from the object, from which the spatial configuration of its internal components or elements can be determined. This is advantageous in several applications. In meat processing in particular relatively sparse depth information may be sufficient to allow the calculation of cuts in automated meat processing operations.

In meat processing applications a large number of carcasses need to be imaged in as short a time as possible. Acquiring a suitable pair of images to generate 3D coordinate data for each object can take a significant amount of time without employing expensive and complex imaging equipment. In meat processing operations cost effectiveness is imperative and switched X-ray sources are prohibitively expensive both in terms of capital cost and regular replacement of switched X-ray sources.

Carcasses often need to be imaged when hanging from a conveyer. Swinging of the carcass or slight variations in velocity can introduce artefacts in associated X-ray images. These artefacts can be compounded when generating 3D coordinate data from suitable pairs of X-ray images, leading to inaccuracies when determining the spatial configuration of the object's internal components or elements.

Double pass systems use a single X-ray source and a single detector. A conveyer conveys objects through the imaging system. In order to acquire two separate images from different perspectives, the object must be conveyed through the imaging system a first time through a first path, and then be conveyed through the same imaging system a second time through a path different to the first. If a carcass swings during the acquisition of either X-ray image, artefacts can be introduced which may degrade the generated 3D data.

Dual X-ray systems use a pair of X-ray sources and a pair of X-ray detectors spaced apart from each other. A conveyer conveys objects through the imaging system, where they are sequentially imaged by each source-detector pair. The duplication of sources and detectors in these imaging systems increases cost and complexity and the spacing between each source-detector pair can create inaccuracies in the final 3D data caused by lateral swing of the object as it is conveyed through the imaging system.

SUMMARY

According to one example embodiment there is provided an X-ray imaging system, including:
a. an X-ray detector,
b. a plurality of X-ray sources, each X-ray source configured to illuminate the X-ray detector from a different perspective,
c. a shutter in a transmission plane between each X-ray source and X-ray detector, wherein the shutter controls the transmission of X-rays from each X-ray source through the transmission plane to the X-ray detector, and
d. a processor in communication with the X-ray detector for receiving and processing X-ray data received from the X-ray detector, and
e. a conveyor configured to convey the object through the transmission plane;
wherein the X-ray imaging system is configured to image the object when the object is positioned between the shutter and the X-ray detector.

There is further provided a method of imaging an object using X-rays, the method including:
a. providing a plurality of X-ray sources,
b. providing a detector configured to be illuminated by the plurality of X-ray sources, wherein each X-ray source illuminates the detector from a different perspective,
c. providing a shutter in a transmission plane between said plurality of X-ray sources and said detector, the shutter controlling the transmission of X-rays to the detector from each X-ray source,
d. providing a conveyor configured to convey the object to be imaged between the shutter and the detector,
e. capturing images of the object with the detector when illuminated by each X-ray source; and
f. developing depth, height and width information using a processor based on analysis of the images.

There is also provided an X-ray shutter for controlling the passage of X-rays in a transmission plane through the shutter, the shutter defining a plurality of transmission paths configured to allow X-rays generated at different positions in the transmission plane to pass through a respective transmission path and being configured such that at most one transmission path is aligned with the transmission plane at any time.

It is acknowledged that the terms "comprise", "comprises" and "comprising" may, under varying jurisdictions, be attributed with either an exclusive or an inclusive meaning. For the purpose of this specification, and unless otherwise noted, these terms are intended to have an inclusive meaning—i.e., they will be taken to mean an inclusion of the listed components which the use directly references, and possibly also of other non-specified components or elements.

Reference to any document in this specification does not constitute an admission that it is prior art, validly combinable with other documents or that it forms part of the common general knowledge.

BRIEF DESCRIPTION OF THE DRAWINGS

The accompanying drawings which are incorporated in and constitute part of the specification, illustrate embodiments of the invention and, together with the general description of the invention given above, and the detailed description of embodiments given below, serve to explain the principles of the invention, in which.

DETAILED DESCRIPTION

Figure 1:
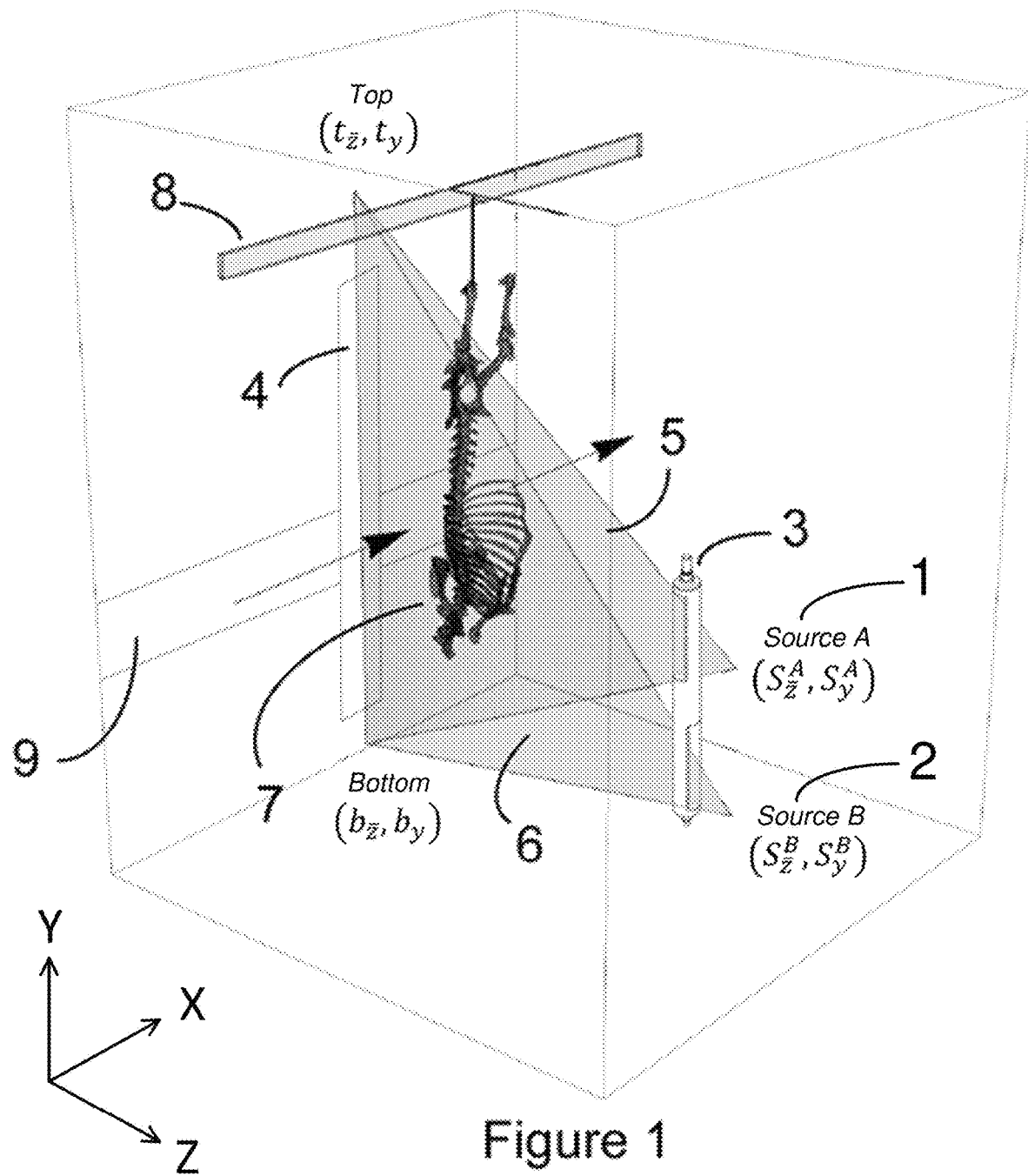
FIG. 1 Shows a perspective view of an X-ray imaging system according to one embodiment.
Figure 2:
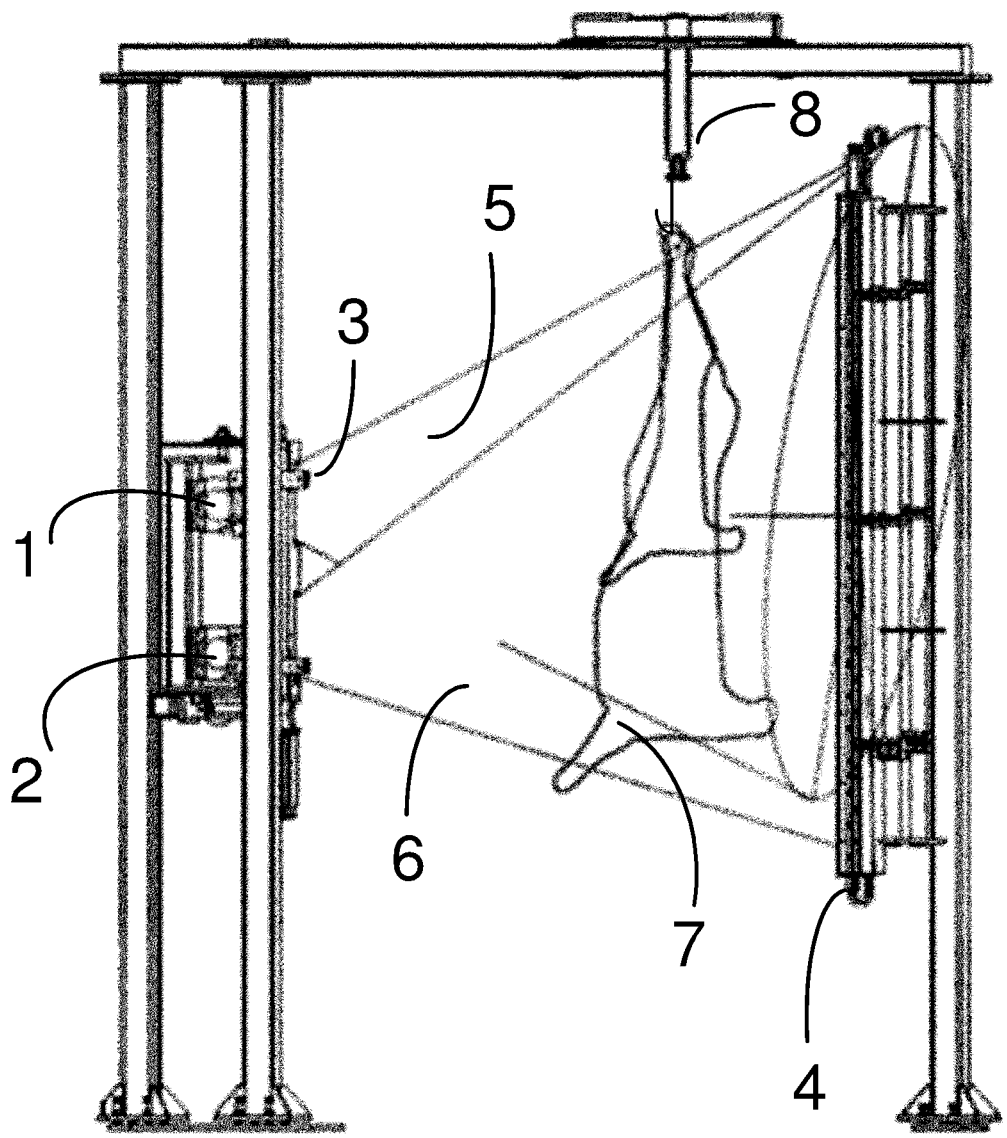
FIG. 2 Shows a side view of the X-ray imaging system of FIG. 1.
Figure 3:
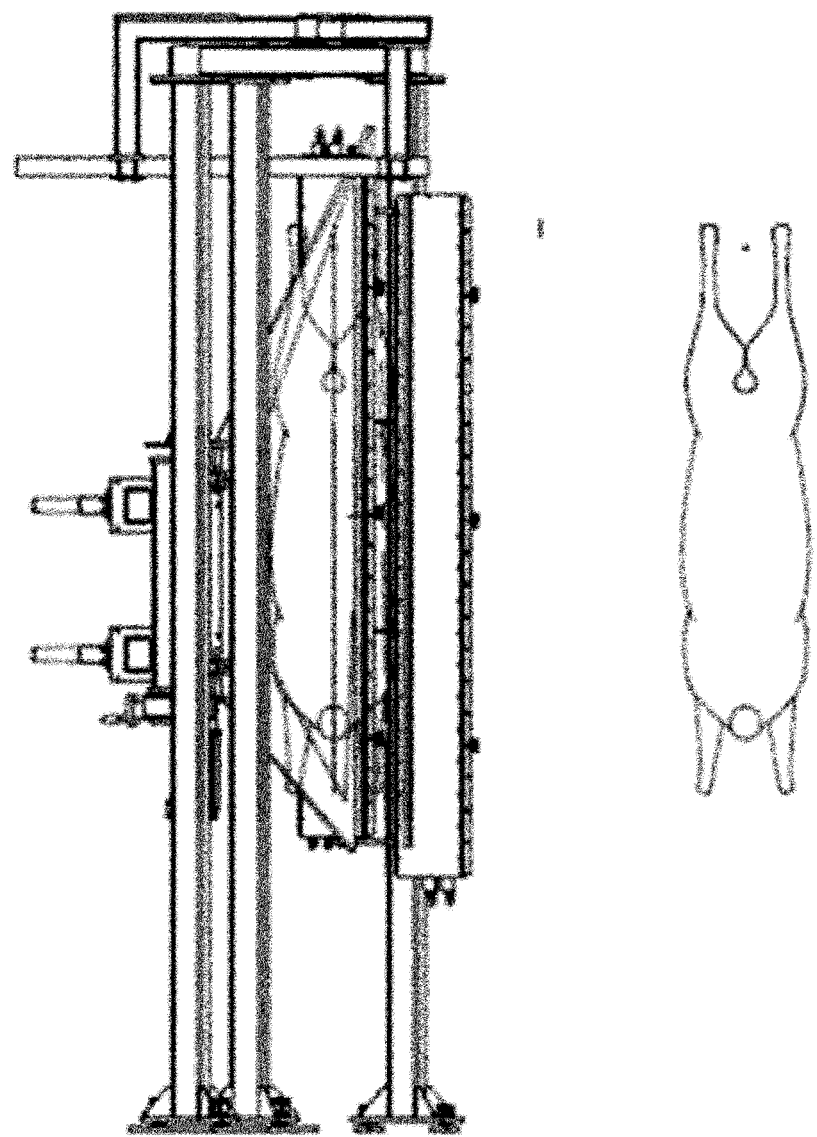
FIG. 3 Shows a front view of the X-ray imaging system of FIG. 1.

FIG. 1 provides a conceptual illustration of an X-ray imaging system according to an example embodiment. FIGS. 2 to 9 provide detail as to the construction and operation of a working embodiment.

In this embodiment two X-ray sources 1 and 2 are provided, although additional X-ray sources may be provided in other applications, for example where imaging is required from more perspectives due to the nature of the object being imaged. A shutter 3 controls the passage of X-rays from sources 1 and 2 to illuminate linear X-ray detector 4 from different perspectives. Although a linear detector is used in this embodiment the detector could be a two dimensional detector or comprise a number of detectors. Where in this specification reference is made to a "detector" this may be a single array of detectors or a multi-dimensional detector array or a number of discrete detectors. The upper section of shutter 3 includes a transmission path which in at least one angular position allows X-rays from X-ray source 1 to pass through the shutter in a fan beam 5 (Fan beam 5 is in fact occluded by the shutter 3 in the particular example illustrated in FIG. 1, but is shown simply to illustrate its path when not occluded. This applies to later drawings too). The lower section of shutter 3 includes a transmission path which in at least one angular position allows X-rays from X-ray source 2 to pass through the shutter 3 in a fan beam 6. Fan beams 5 and 6 lie substantially in a common plane referred to as the "transmission plane" between the sources 1 and 2 and the detector 4. In other words, the shutter 3 defines a plurality of transmission paths which allow X-rays generated at different positions in the transmission plane to pass through the shutter 3.

The shutter 3 rotates to align transmission paths for the first X-ray source 1 and the second X-ray source 2 with the transmission plane. In this embodiment the transmission paths of the shutter 3 are angularly offset about the axis of rotation of shutter 3 so that fan beams 5 and 6 alternately illuminate detector 4. The shutter 3 may be configured so that at most one transmission path is aligned with the transmission plane at any time. This arrangement means that the X-ray sources 1 and 2 may be continually powered, thus avoiding degradation due to constant switching, and allowing very fast scan rates of 3.3 milliseconds per scan line. The mechanical arrangement of the rotating shutter provides a robust and inexpensive means of alternating the beams allowing rapid imaging.

From an adjacent pair of images (or "scanlines") produced by detector 4 depth and height information may be obtained for points of interest using stereoscopic analysis techniques as explained more fully later in this specification. As a carcass 7 is conveyed by conveyor 8 through the transmission plane a series of pairs of such one dimensional images are obtained which may be compiled to form two 2D data sets of the same carcass from two different perspectives and/or a 3D data coordinate set (this is typically a data set of selected points of interest not including all known x/y data points).

To limit carcass swing a stabiliser belt 9 may be provided that moves with the conveyor and supports the carcass against swing. Alternatively, or additionally, a hock stabiliser and/or a static rub-rail (along the back of the carcass) could be used to restrain lateral movement of a carcass.

Figure 5:
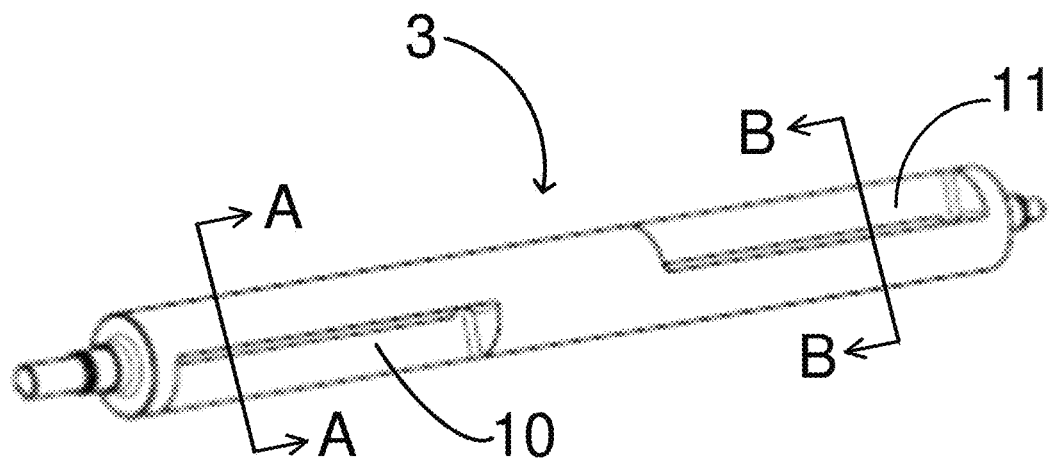
FIG. 5 Shows a shutter used in the X-ray imaging system of FIG. 1.
Figures 6, 7:
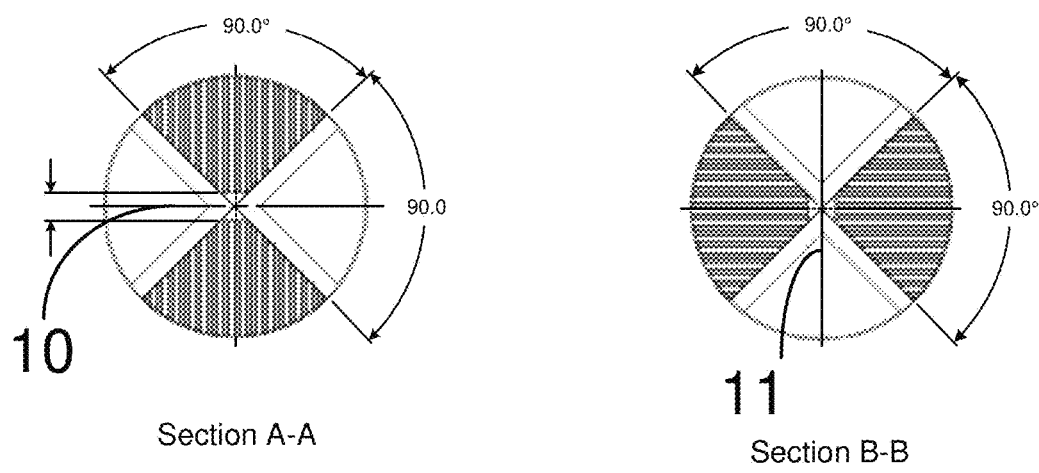
FIG. 6 Shows a cross sectional view through line A-A in FIG. 5.
FIG. 7 Shows a cross sectional view through line B-B in FIG. 5.

Referring to FIGS. 5 to 7 the shutter 3 is shown in more detail. FIG. 6 shows a cross-section through line A-A in FIG. 5 illustrating the transmission path 10 provided in the lower part of shutter 3. FIG. 7 shows a cross-section through line B-B in FIG. 5 illustrating the transmission path 11 provided in the upper part of shutter 3. It will be noted that the transmission paths 10 and 11 are orthogonal to each other so that as the shutter rotates fan beams 5 and 6 alternately illuminate the detector 4. It will be appreciated that additional transmission paths could be provided to increase the number of scans per revolution of the shutter.

Figure 8:
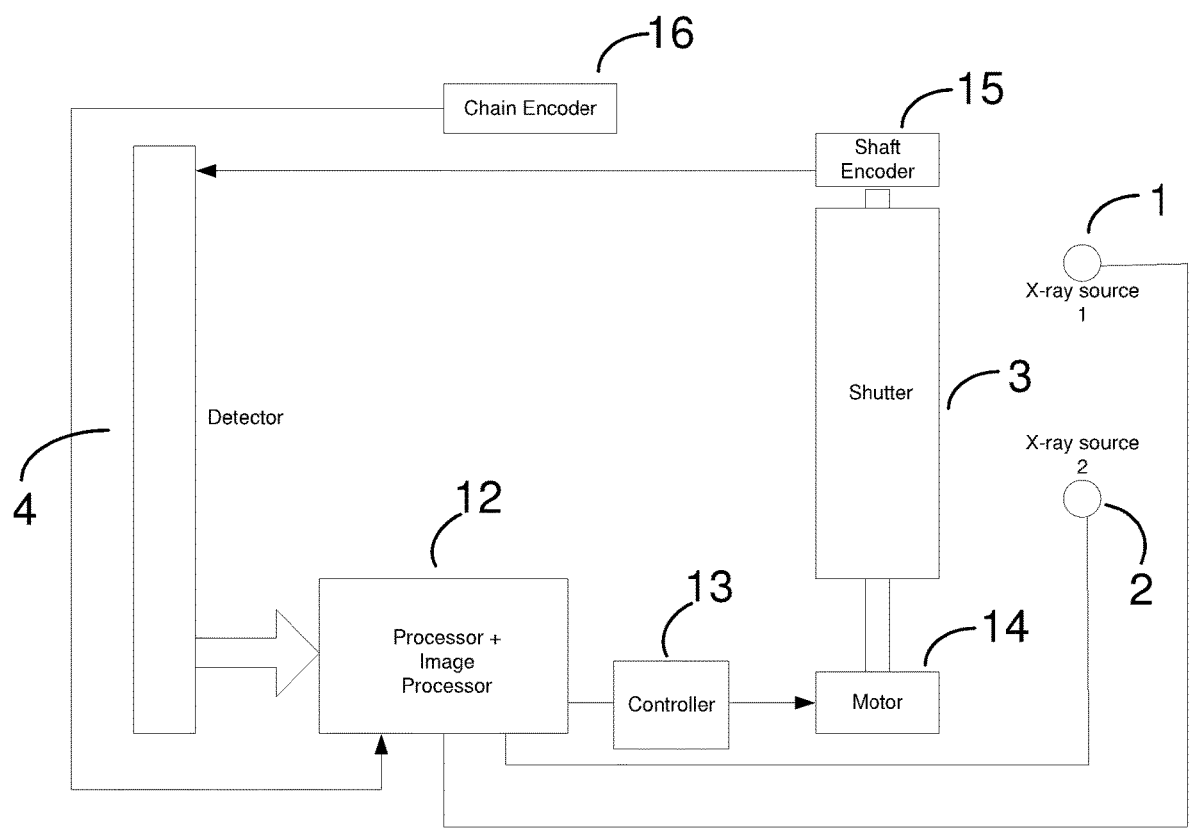
FIG. 8 Shows a block diagram of the control system and imaging processor of the X-ray imaging system of FIG. 1.

Referring now to FIG. 8 the control and imaging systems will be described. A processor 12 includes hardware control and image processing functions. This may be a general purpose computer or application specific processor. Processor 12 controls the operation of a controller 13, which may be a programmable logic controller (PLC) or the like, which controls motor 14 to rotate shutter 3 about its axis. The shutter may rotate at a speed of about 4,500 rpm so that the detector may obtain 150 scans/second for each X-ray source. This may allow imaging of about 10 carcasses per minute with a scanline every 0.5 mm of conveyor travel. A rotational speed of greater than at least 100 rpm is considered necessary for a practical meat processing solution. An angular position detector 15, such as a rotary encoder or Hall effect detector, detects when transmission paths of the shutter are aligned with the transmission plane and sends a signal to the detector which outputs the image acquired at that time to the processor 12. A chain encoder 16 provides information as to speed of the conveyor so that successive one dimensional images (scanlines) may be stitched together with the proper spacing.

Figure 4A:
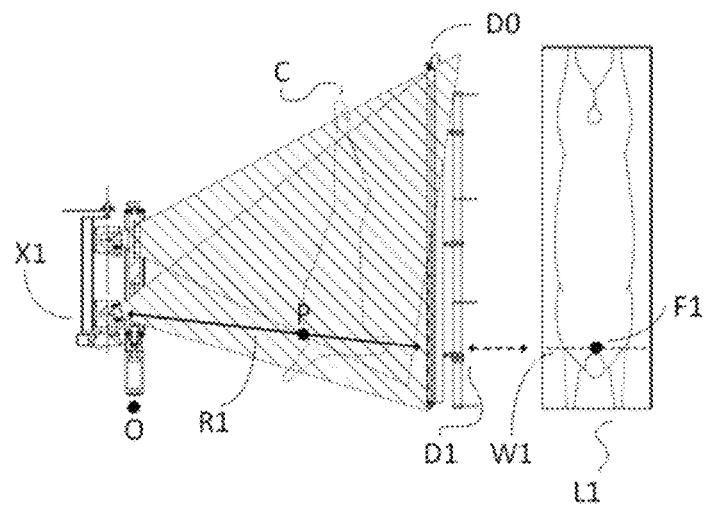
FIG. 4 Illustrates how depth information is determined using the X-ray imaging system of FIG. 1.
Figure 4B:
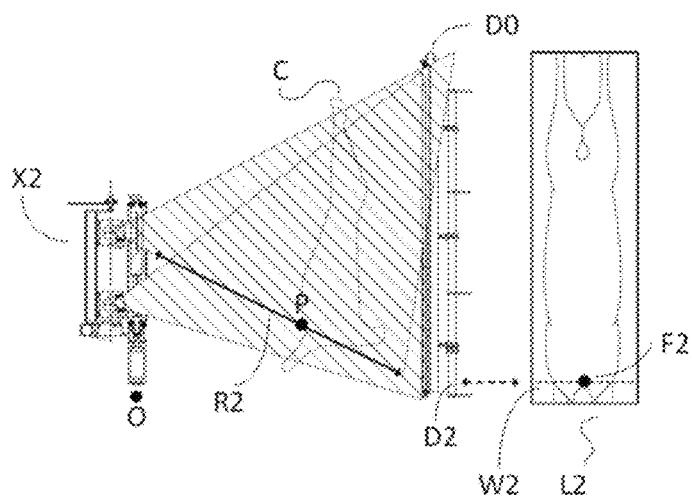
Figure 4C:
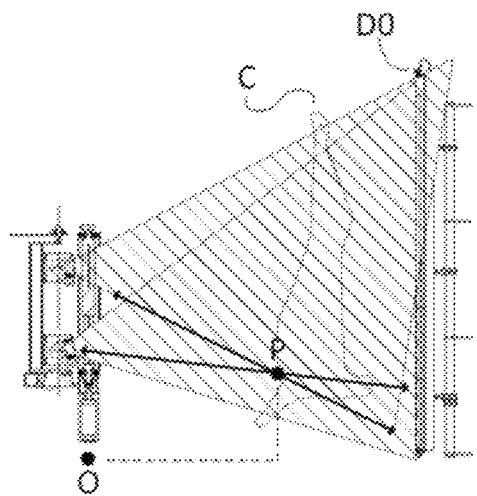

Referring to FIGS. 4a to 4c one method for developing depth information for points of interest will be described. Each carcass 7 is alternately imaged line-by-line by the X-ray sources as it is conveyed through the X-ray imaging system. The shutter 3 first exposes the carcass to radiation from first X-ray source 1 for a period of time, and then obscures the first X-ray source to allow the detector to output its detected image to the processor. The shutter system then exposes the carcass to the second X-ray source 2, and the process is repeated. The carcass is imaged line-by-line alternatingly by each X-ray source in this fashion until the entire carcass is conveyed past the detector 4 and imaged.

Figure 10:
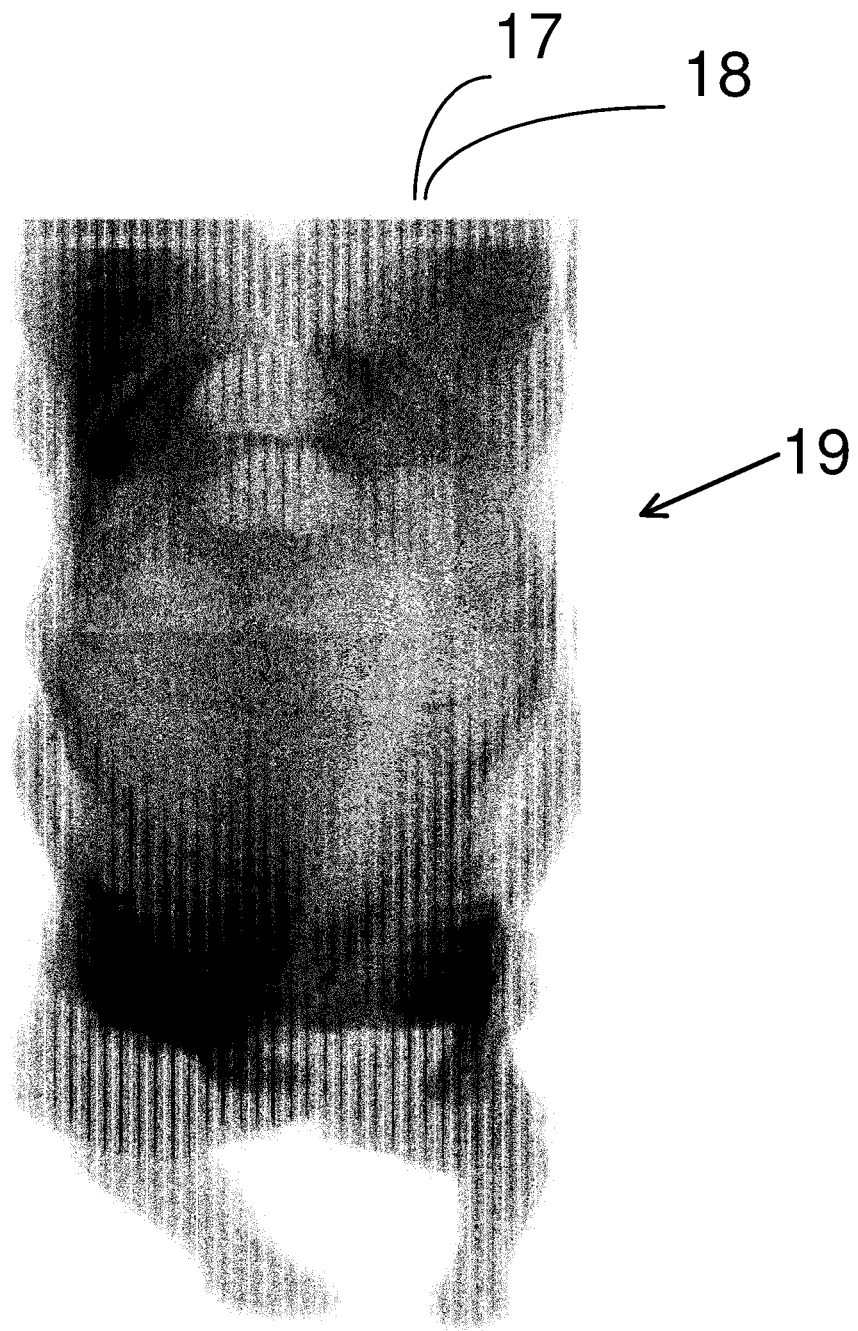
FIG. 10 Illustrates the acquisition of alternating image slices using the X-ray imaging system of FIG. 1.

The processor 12 continually timestamps and appends each scanline outputted by the detector to a data set (which could be graphically viewed as a composite interlaced image as per illustrative FIG. 10). Because the object is alternately imaged with each X-ray source, and each X-ray source is at a different position from the detector, the even-numbered columns of pixels of the interlaced image are linescans imaged from one perspective, while the odd-numbered columns of pixels of the interlaced image are linescans imaged from an alternative perspective.

FIG. 10 is a simplified illustration of a carcass 19 to show alternate one dimensional images 17 and 18 ("scanlines") associated with different X-ray sources. In a real system scanlines may be obtained at about every 0.5 mm of travel. Whilst the description below refers to "images" for ease of comprehension it will be appreciated that in meat processing applications what is produced is data sets that may include coordinates only for points of interest which are used to guide automated processing equipment. This may be a subset of coordinates defined in three dimensional space.

To convert the interlaced image into the required 3D data coordinates, the processor first separates the interlaced image (see FIG. 10) into two or more separate images, each image corresponding to each of the X-ray sources. Processor 12 may determine the boundaries of an image by detection of null zones on either side of a sequence of scanlines (i.e. areas in which no scanned object is present). This can be achieved, for example, by separating the evenly-numbered rows of pixels and the oddly-numbered rows of pixels into two separate images, in the case of two X-ray sources. Each separated or de-interlaced image depicts the entire carcass imaged from the perspective of a single respective X-ray source. Alternatively, if more than two X-ray sources are used, the interlaced image can be separated by every third column of pixels in the case of three X-ray sources, et cetera.

Having separated the interlaced image into multiple constituent images, the processor then performs image analysis to identify and match features on the carcass shared by the images. This image analysis can be achieved using existing methods known to those skilled in the art. As a non-limiting example, the processor may utilise edge detection, corner detection, or thresholding to identify and match common features between the two images. Edge detection in particular is advantageous as each pixel on the detector represents a ray which has travelled through an entire volume of the carcass, which can blur individually distinguishable features. In contrast, sharp and well-defined edges can be identified and matched with relative ease.

Once a feature has been identified and matched in each image, the processor then determines the row of pixels where that feature occurs in each respective image. The row of pixels in an image directly corresponds to a discrete detection element on the detector in real space. Therefore, if the geometric and positional relationship between the X-ray sources and the detector is accurately known, a ray can be computed from a given row of discrete detection element on the detector to an originating X-ray source. A convenient origin for the local coordinate system is also chosen using a well-known position on the imaging system, such as one of the X-ray sources, or the base of one of the shutter parts.

A given feature will appear on a different row of pixels in each of the separated images, and the processor computes rays from each of those rows of pixels to their respective X-ray sources. The processor then computes the intersection of those rays, which accurately gives the depth and height measurements (or y and z coordinates) of that feature on the physical carcass with respect to the local origin. The processor then uses the velocity of the carcass provided by conveying means, and the timestamp appended to each individual linescan, to calculate the width (or x coordinate) of the given feature on the physical carcass.

FIG. 4 shows an exemplary embodiment of determining the coordinates of a point from two separated X-ray images. The transmission of X-rays from X-ray source X1 through a point P on a carcass C creates a feature F1 on separated X-ray image L1, as shown in FIG. 4a. The processor 12 identifies this feature and determines the row of pixels W1 in the image L1 where the feature F1 is present. The row of pixels W1 directly corresponds to a row of detection elements D1 on detector D0. Using the knowledge that the image L1 was taken using X-ray source X1, and the positional relationship between detector DO and X-ray source X1, the processor computes a ray R1 from detection elements D1 to X-ray source X1 which passes through point P.

Similarly, the transmission of X-rays from X-ray source X2 through the same point P on the carcass C creates a feature F2 on X-ray image L2, which the processor identifies and matches through image analysis. Because X-ray image L2 is acquired using X-ray source X2, which is at a different position to P relative to X1, the corresponding feature F2 on image L2 appears in a different row of pixels W2, as shown in FIG. 4b. The processor determines the row of pixels W2 and their directly corresponding detection elements D2. The positional relationship between elements in the imaging system is used to compute a ray R2 from detection elements D2 to X-ray source X2 which also passes through point P.

Having computed rays R1 and R2, the processor then computes their intersection, as shown in FIG. 4c. The computation of the intersection gives the distance and height (or y and z coordinates) of point P relative to a known origin O, here shown for simplicity at the base of the shutter system.

Figure 9:
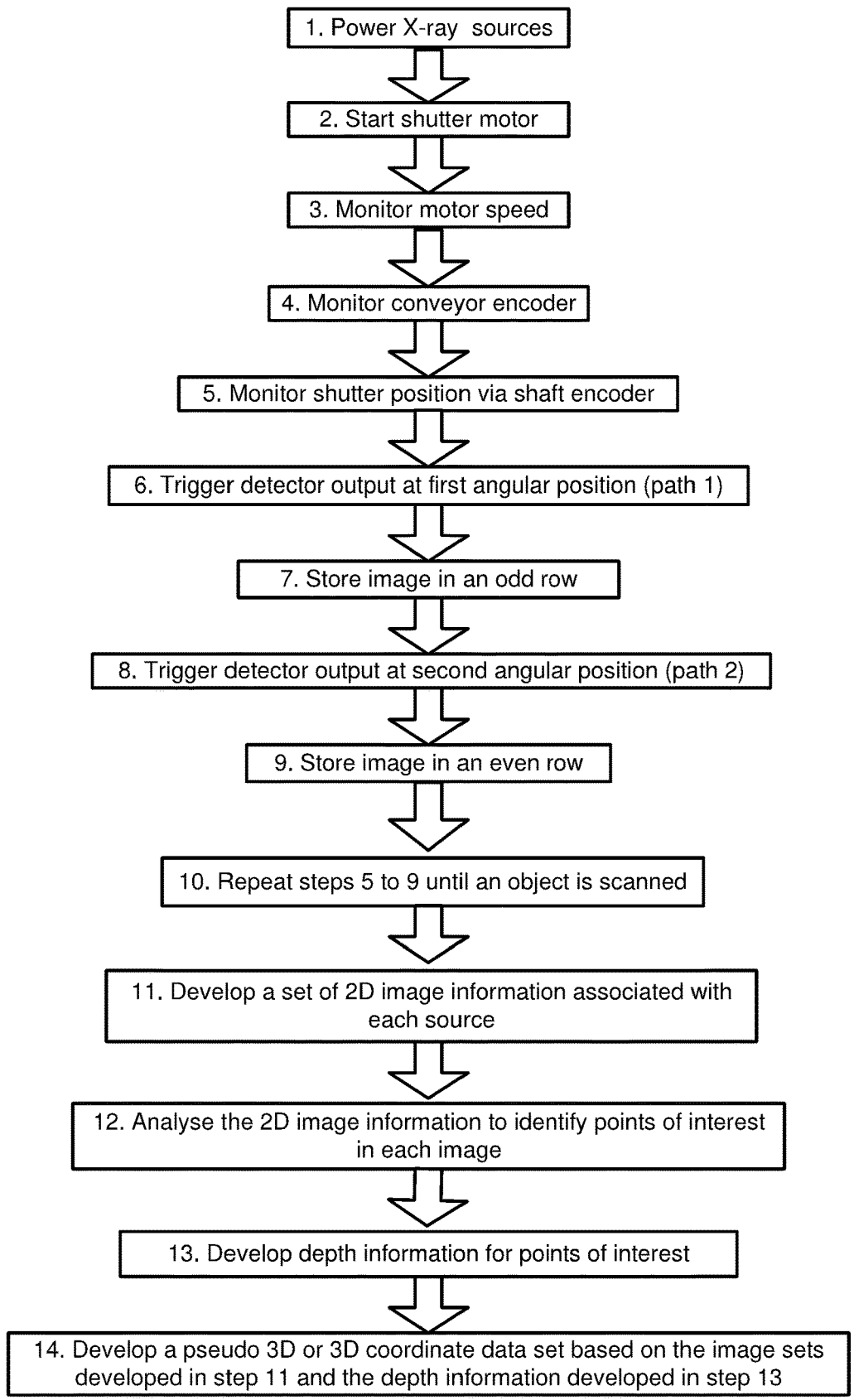
FIG. 9 Shows a flow diagram of operation of the X-ray imaging system of FIG. 1.

FIG. 9 illustrates an exemplary process for developing 3D coordinate data using the imaging system described above.

Figure 11:
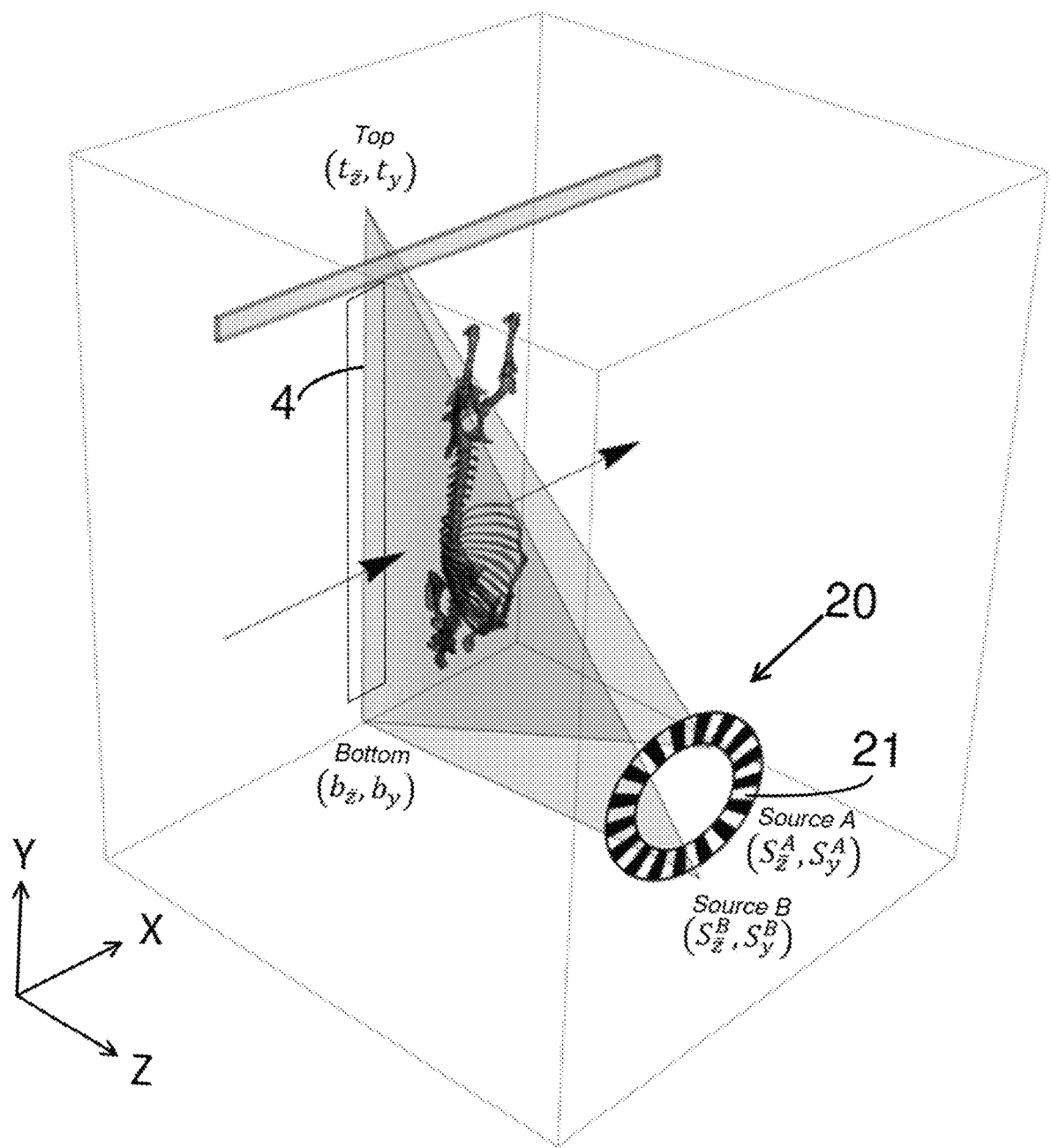
FIG. 11 Shows an X-ray imaging system employing a first alternate shutter.

FIG. 11 shows a conceptual view of an X-ray imaging system as per the previous embodiment but employing an alternative shutter system 20. In this case the shutter rotates about a horizontal axis so that apertures 21 (only one indicated) alternatively illuminate detector 4.

Figure 12:
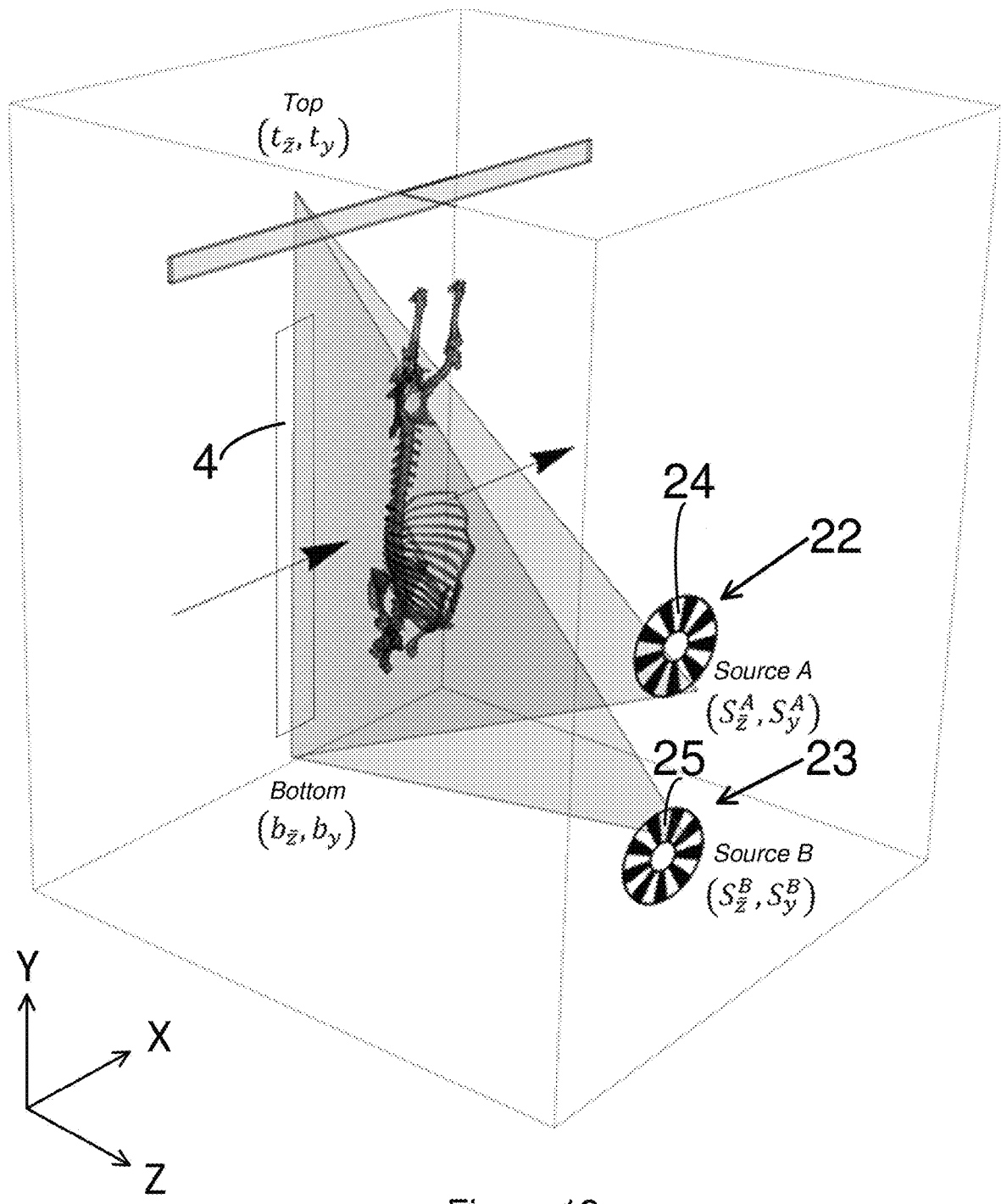
FIG. 12 Shows an X-ray imaging system employing a second alternate shutter.

In a further embodiment shown in FIG. 12 a pair of rotating shutters 22 and 23 with apertures 24 and 25 are synchronised so as to alternately illuminate detector 4. The shutters 22 and 23 may be mechanically linked (by gears etc.), or electronically controlled to ensure synchronisation.

Figure 13:
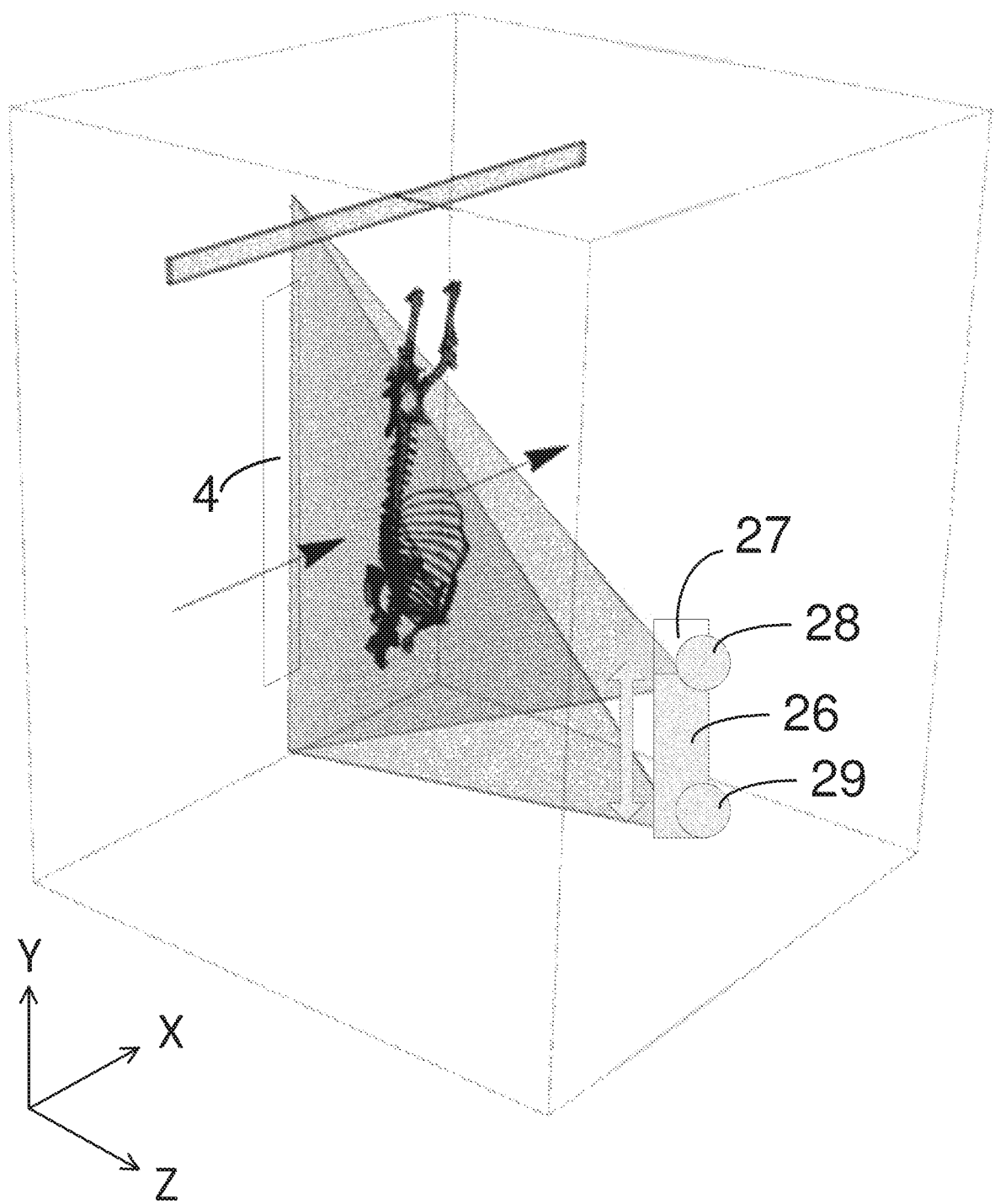
FIG. 13 Shows an X-ray imaging system employing a third alternate shutter.

FIG. 13 shows a further embodiment in which a shutter 26 translates between a first position (shown) in which an opening 27 allows a first source 28 to illuminate detector 4 whilst the second source is blocked and a second position (when the shutter 26 moves up) in which an opening is formed at the bottom to allow second source 29 to illuminate detector 4 whilst the first source 28 is blocked.

In summary, the systems, methods, and apparatus disclosed here offer an inexpensive, fast, and accurate means for generating coordinate data suitable for 3D or pseudo-3D images of objects using X-rays. The system is particularly suited to use in the meat processing industry for imaging ovine, bovine, porcine, equine, or poultry carcasses. The systems and methods are compatible with a single linear detector, reducing the overall cost of the system, although are also compatible with multiple detectors if desired. Switching and power cycling of X-ray sources is avoided, drastically increasing the throughput of imaging objects without the need for expensive fast-switching sources. Furthermore, the impact of errors and artefacts introduced in the 3D or pseudo-3D images by swinging or uncontrolled motion of the object is reduced, producing high-quality and accurate images without the need to reduce the rate of objects conveyed through the imaging station or to implement expensive stabilisation equipment.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

The invention claimed is:

1. An X-ray imaging system, including:
   a. an X-ray detector,
   b. a plurality of X-ray sources, each X-ray source configured to illuminate the X-ray detector from a different perspective,
   c. a shutter in a transmission plane between each X-ray source and the X-ray detector, wherein the shutter controls a transmission of X-rays from each X-ray source through the transmission plane to the X-ray detector,
   d. a processor in communication with the X-ray detector for receiving and processing X-ray data received from the X-ray detector, and
   e. a conveyor configured to convey an object through the transmission plane; wherein the X-ray imaging system is configured to image the object when the object is positioned between the shutter and the X-ray detector; and
   wherein the plurality of X-ray sources comprises two X-ray sources, wherein the shutter alternatingly allows the transmission of X-rays from the two X-ray sources through the transmission plane.

2. An X-ray imaging system as claimed in claim 1, wherein the shutter is a rotating shutter.

3. An X-ray imaging system as claimed in claim 2, wherein:
   the shutter has a plurality of transmission paths through the shutter, and
   each transmission path is angularly offset with respect to the other transmission paths about an axis of rotation of the shutter.

4. An X-ray imaging system as claimed in claim 1, wherein the shutter rotates at a speed greater than 100 rpm.

5. An X-ray imaging system as claimed in claim 1, wherein the shutter is a translating shutter.

6. An X-ray imaging system as claimed in claim 1, further including at least one stabiliser to limit swinging of a carcass.

7. An X-ray imaging system as claimed in claim 6, wherein the at least one stabiliser is a belt or a rub rail restraining a lateral movement of a carcass.

8. An X-ray imaging system as claimed in claim 6, wherein the at least one stabiliser is a hock stabiliser restricting a lateral movement of a carcass.

9. An X-ray imaging system as claimed in claim 1, wherein the X-ray detector is a linear X-ray detector.

10. An X-ray imaging system as claimed in claim 1, wherein at least one of the plurality of X-ray sources operates continuously.

11. An X-ray imaging system as claimed in claim 1, wherein at least one of the plurality of X-ray sources is a fan beam source.

12. An X-ray imaging system, including:
    a. an X-ray detector,
    b. a plurality of X-ray sources, each X-ray source configured to illuminate the X-ray detector from a different perspective,
    c. a shutter in a transmission plane between each X-ray source and the X-ray detector, wherein the shutter controls a transmission of X-rays from each X-ray source through the transmission plane to the X-ray detector,
    d. a processor in communication with the X-ray detector for receiving and processing X-ray data received from the X-ray detector, and
    e. a conveyor configured to convey an object through the transmission plane;
    wherein the X-ray imaging system is configured to image the object when the object is positioned between the shutter and the X-ray detector; and
    wherein the processor is configured to develop depth, height, and width information based on an analysis of X-ray images received from the X-ray detector.

13. An X-ray imaging system as claimed in claim 12, wherein the processor is configured to:
    i. identify at least one feature of an object in each of a plurality of X-ray images,
    ii. match the at least one feature of the object in each of the plurality of X-ray images,
    iii. for each X-ray image of the plurality of X-ray images, determine a position on the X-ray detector corresponding to coordinates of the at least one feature of the object in each X-ray image, and
    iv. combine the positions on the X-ray detector to determine three-dimensional coordinates of a point of the object, which corresponds to the at least one feature of the object.

14. An X-ray shutter for controlling a passage of X-rays in a transmission plane through the X-ray shutter, the X-ray shutter comprising:
    a body defining a plurality of transmission paths configured to allow X-rays generated by different X-ray sources at different positions in the transmission plane to pass through a respective transmission path;
    wherein the body is configured such that at most one transmission path of the plurality of transmission paths is aligned with the transmission plane at any time; and
    wherein the plurality of transmission paths are alternately aligned with the transmission plane.

15. An X-ray shutter as claimed in claim 14, wherein the body rotates to align different transmission paths with the transmission plane.

16. An X-ray shutter as claimed in claim 15, wherein:
    each transmission path is angularly offset with respect to the other transmission paths about an axis of rotation of the body.

17. An X-ray shutter as claimed in claim 14, wherein the body translates to define the plurality of transmission paths.

18. An X-ray shutter as claimed in claim 14, wherein the body is a single moving element, which controls the plurality of transmission paths.

* * * * *